United States Patent [19]

Peschmann

[11] Patent Number: 4,531,226
[45] Date of Patent: Jul. 23, 1985

[54] MULTIPLE ELECTRON BEAM TARGET FOR USE IN X-RAY SCANNER

[75] Inventor: Kristian R. Peschmann, San Francisco, Calif.

[73] Assignee: Imatron Associates, South San Francisco, Calif.

[21] Appl. No.: 476,425

[22] Filed: Mar. 17, 1983

[51] Int. Cl.³ .......................... H01J 1/00; H01J 35/08
[52] U.S. Cl. ..................................... 378/143; 313/237
[58] Field of Search ...................... 378/143, 4, 10, 11, 378/12, 14; 313/237; 445/2, 61, 67

[56] References Cited

U.S. PATENT DOCUMENTS 2,640,924  6/1953  McMillan ............................ 378/143
4,274,005  6/1981  Yamamura ........................... 378/10
4,352,021  9/1982  Boyd .................................... 378/12

Primary Examiner—Alfred E. Smith
Assistant Examiner—Charles F. Wieland
Attorney, Agent, or Firm—Flehr, Hohbach, Test, Albritton & Herbert

[57] ABSTRACT

Disclosed is a target structure for use in an X-ray transmission scanner in which X-rays are generated by directing an electron beam at an X-ray generating target. The structure includes a support bracket having a recessed portion and a support surface formed in the recessed portion. A bolt extends through the bracket and maintains a target member in abuttment with the support surface which positions the target in proper alignment with an electron beam.

8 Claims, 6 Drawing Figures

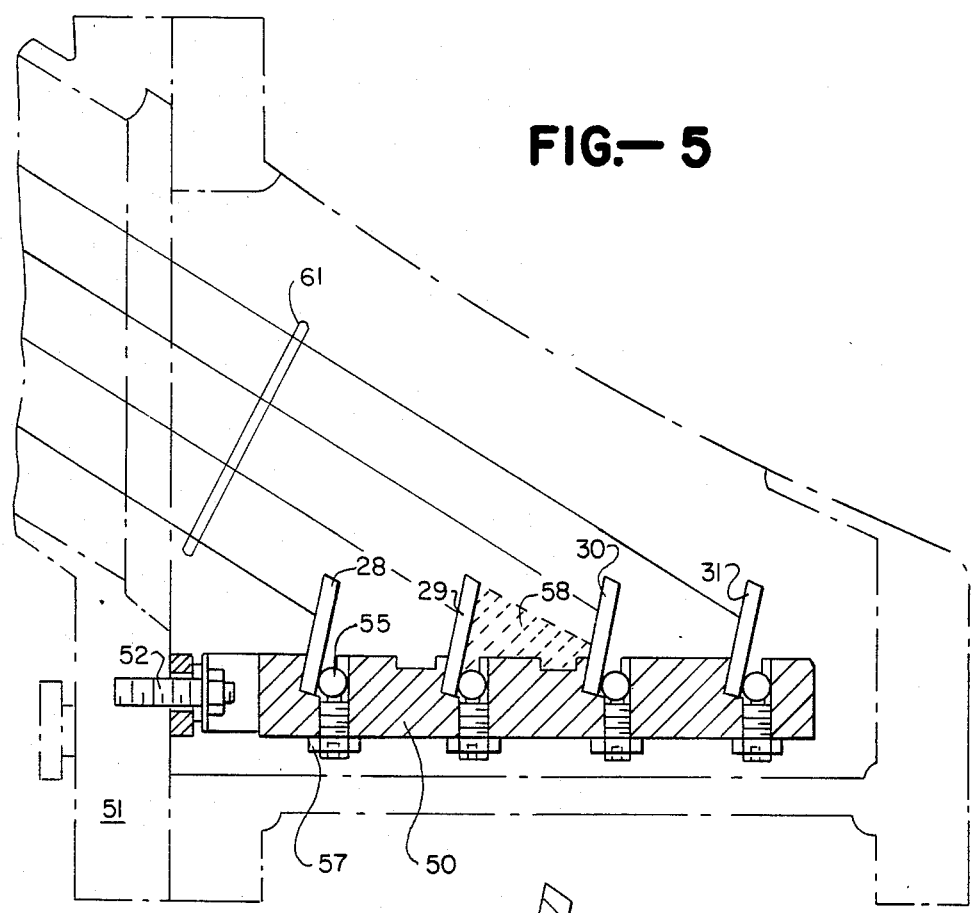
FIG.—5
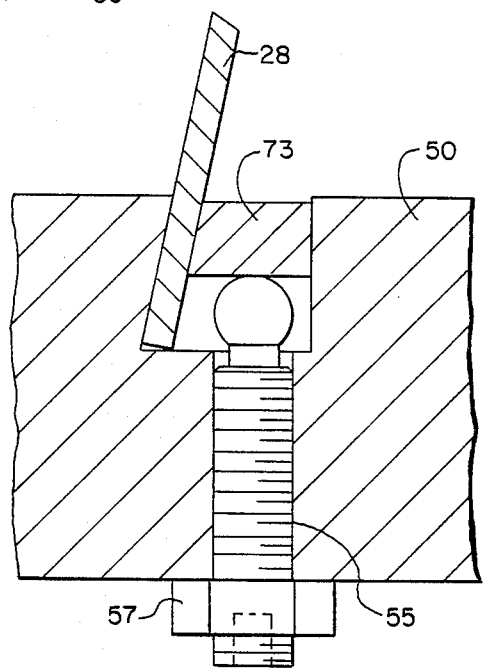
FIG.—6

MULTIPLE ELECTRON BEAM TARGET FOR USE IN X-RAY SCANNER

This invention relates generally to a high speed multiple section computed-tomographic (CT) medical scanning system, and more particularly the invention relates to an electron beam target structure for use therein.

Disclosed in U.S. Pat. No. 4,352,021 is a high speed X-ray scanning system in which the X-ray source and the X-ray detectors are stationary and a plurality of fan beams of radiation is generated by sweeping an electron beam across a plurality of targets arcuately arranged whereby each target generates radiation fan beams.

The electronic scanning system incorporates a single electron beam tube. The electron beam is deflected by suitable magnetic and/or electric fields to produce a movable X-ray source on one of four adjacent semi-circular target rings to provide scanning fan beams that can be used to image an entire volume of tissue in multiple sections. Such an electronic scanning system is vastly superior in speed to the mechanical scanning systems in the prior art referenced in U.S. Pat. No. 4,352,021. Fraction-of-a-second scan time of a volume can be achieved as compared to one or more seconds required for the mechanical scan of a single section. The system eliminates the need for moving parts that require high precision and alignment. In addition, elaborate systems of sliding electrical contacts are eliminated. The scanner is an improvement over that shown and described in U.S. Pat. No. 4,158,142, in that it permits nearly simultaneous viewing multiple sections of the body which may encompass a region as large as the heart. The scanner can provide as many as eight sections.

The system employs a plurality of detectors mounted opposite the target rings. The detectors are arranged in two adjacent partial-circular ring arrays. Each of the arrays contains a multiplicity of detectors as, for example, 444 detectors each, providing a total of 888 detectors. The angular separation of two adjacent detectors is in the order of 0.5 degrees resulting in very high resolution. The scanning system is provided with collimators both for the X-ray source and for the detectors. The source collimator provides a fan-shaped beam 30° of which covers the body with a 30° opening angle. The detector collimators provide interchangeable options: dual section detector arrays, single section detector arrays and high resolution single section detector arrays. A variety of scanning modes can be selected with up to eight sections being scanned at a rate of at least one scan per second.

A problem encountered in the described system results from the high temperatures of the electron beam target which can cause burnout or degraded X-ray sources. Typically, the electron beam current is one ampere at 120 Kv, and should the electron beam scan be stopped, a target on which the beam impinges would be melted. Thus, a need exists for an improved target structure which can be readily replaced.

Accordingly, an object of the present invention is an improved high speed X-ray scanning system.

Another object of the present invention is an improved target for use in a scanned electron beam X-ray system.

Still another object of the invention is a multiple target structure in which individual targets can be readily and accurately replaced.

A further object of the invention is an inexpensive target structure which is easily manufactured, assembled, and maintained.

A feature of the invention is a clamp arrangement for planar target members which facilitates accurate and rigid positioning of the targets.

Briefly, the target structure in accordance with the invention includes an arcuate frame and a plurality of support brackets extending therefrom. Each support bracket has at least one recessed portion including one inclined surface at an angle required by the surface of an electron beam target. The electron beam target comprises a member having a planar surface. The member is supported in the recessed portion with the planar surface engaging the inclined recessed wall. Fastening means engages the target and maintains the planar surface of the target in forced engagement with the inclined recessed surface. The fastening means accommodates targets of various thicknesses and allows for thermal expansion of the targets. Further, each target can be readily replaced in the field. Advantageously, in a multiple target arrangement each target shields the support bracket from the electron beam thereby reducing heat and minimizing damage to the bracket.

The invention and objects and features thereof will be more readily apparent from the following detailed description and appended claims when taken with the drawing, in which:

FIG. 5 is a section view of the targets of FIG. 4 illustrating the mounting of the targets in the system in accordance with one embodiment of the invention.

FIG. 6 is a section view of a target illustrating the mounting of the target in accordance with another embodiment of the invention.

Figure 1:
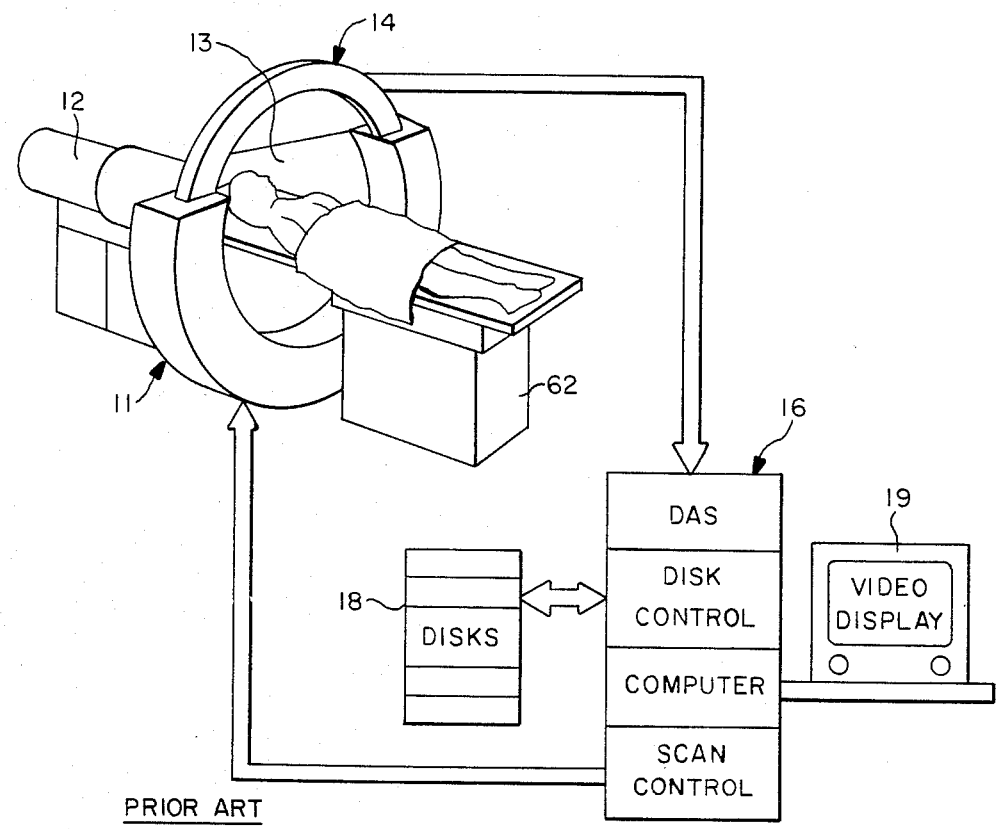
FIG. 1 is a schematic diagram partly in perspective showing a computed tomographic X-ray transmission scanning system employing multiple electron beam targets.

Referring to FIG. 1, the system of U.S. Pat. No. 4,352,021 is seen to include three major components: a scan tube 11 including a cylindrical portion 12, and a semi-circular conical portion 13; a detectory array 14; and, a computer system 16. The scan tube projects an electron beam to target rings which generate X-rays. The X-rays are intercepted by the detector array 14. The output of the detector array is applied to the computer system 16. The computer system includes a plurality of storage discs 18 for recording the data for later processing. The computer system also includes an output which controls the scan tube. A video display 19 presents the data.

Figure 2:
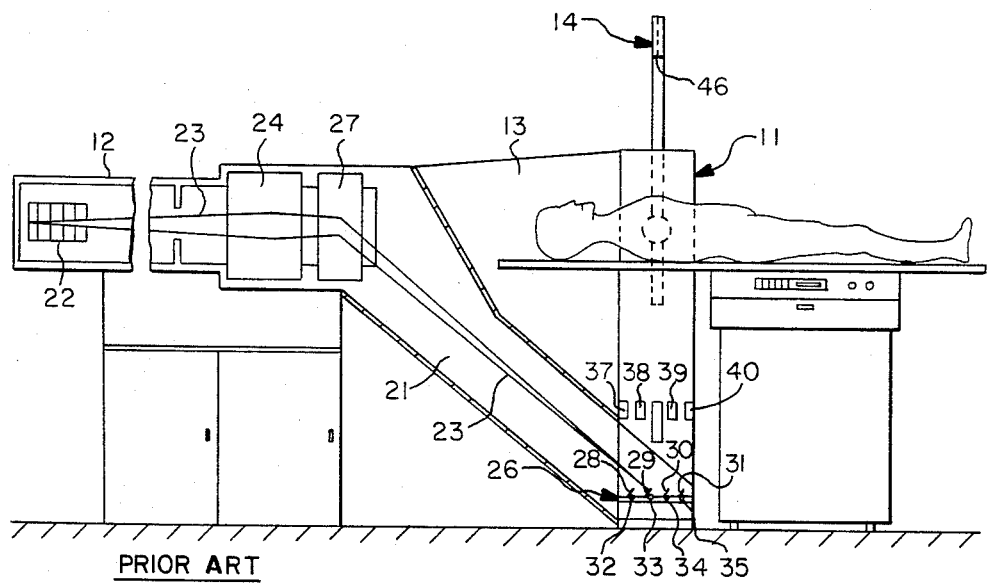
FIG. 2 is a cross section view of the system of FIG. 1.
Figure 3:
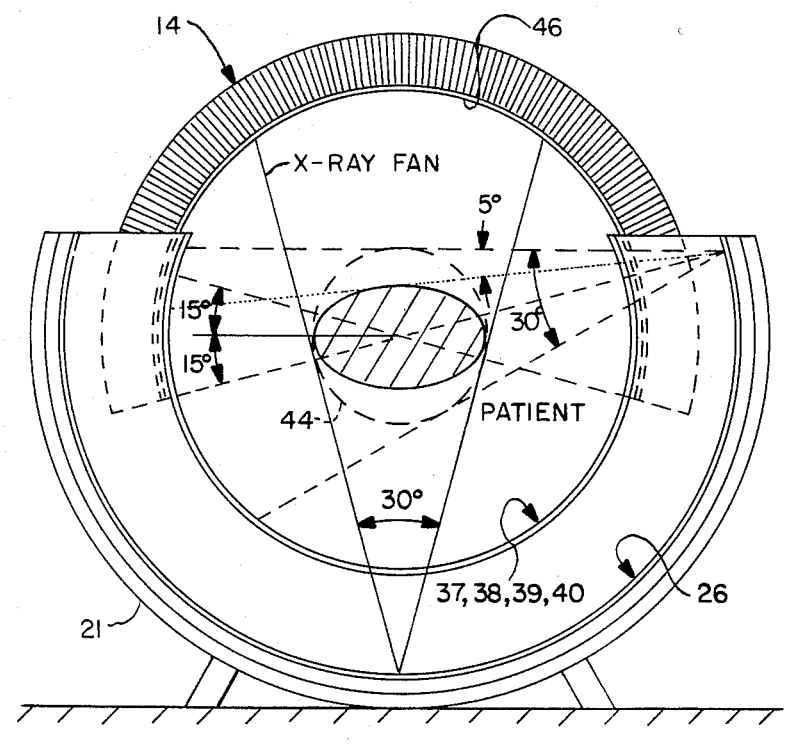
FIG. 3 is an end view of the system of FIG. 1.

Referring more particularly to FIGS. 2 and 3, the scanning system and detection system is shown in more detail. The electron beam tube 11 includes a vacuum envelope 21 which houses an electron gun 22 at the cylindrical end 12. The electron gun projects an axial electron beam 23 along the cylindrical portion. The focus coils 24 focus the beam onto targets 26. Bending coils 27 bend the beam so that it fans out along the partial-circular conical portion of the tube to impinge upon the partial-circular target rings. The target assembly 26 includes a plurality of partial-circular target rings 28, 29, 30 and 31. Suitable cooling coils 32, 33, 34 and 35 are associated with each of the target rings 28, 29, 30 and 31 respectively and serve to cool the target rings.

The bending magnets not only deflect the beam but rapidly sweep it along the partial-circular targets shown in FIGS. 2 and 3. The target rings are scanned serially to obtain a multiple section examination as will be presently described. Ring collimators 37, 38, 39 and 40 are disposed to intercept X-rays emitted by the target rings and define an X-ray beam projected as a one or two centimeter thick planar beam. A fan-shaped sector of this beam is passed through a detector collimator 46 and is detected by the curved detector array and the measured values are utilized to reconstruct a tomographic image of the region 44.

Figure 4:
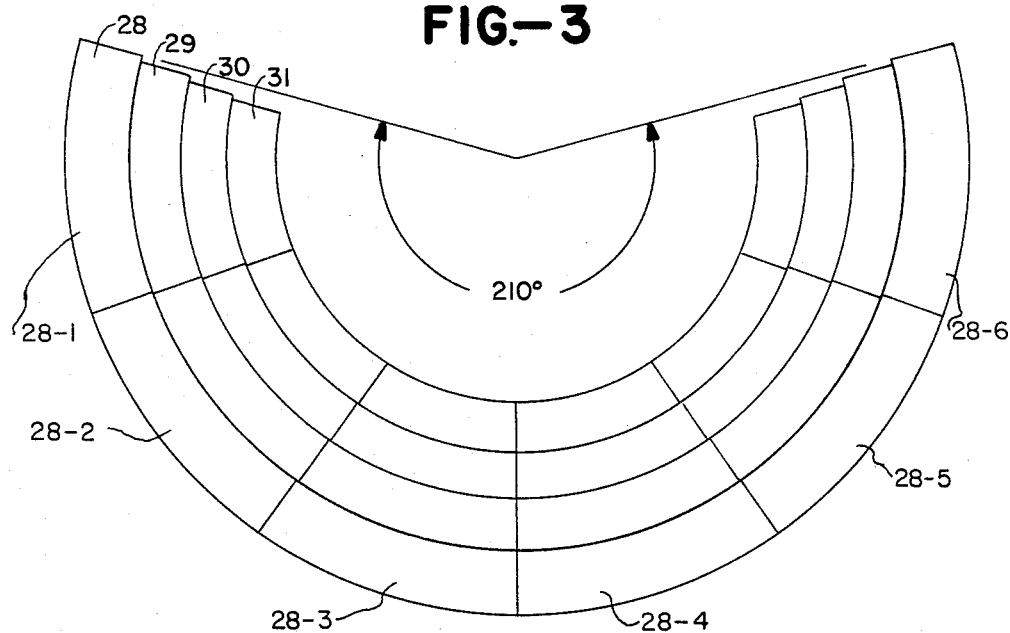
FIG. 4 is a perspective view of electron beam targets in accordance with one embodiment of the present invention.

As described above, the electron beam which impinges on the targets is approximately one ampere of current at 120 Kv voltage and generates substantial heat in the target. The present invention is directed to an inexpensive target structure which is readily assembled in the system for ease in maintenance and replacement. FIG. 4 is a perspective view of the targets 28–31 each of which is arcuate in configuration (e.g. 210°) and comprises a plurality of segments such as the six segments 28-1 through 28-6 for the target 28. Each segment may be solid tungsten sheet or a mounting substrate such as OFHC copper on which a tungsten layer is deposited by plasma spray or to which a tungsten sheet is brazed. Other X-ray emitting surface material, such as tantalum and molybdenum, may be used.

FIG. 5 is a section view illustrating the support structure for the targets 28–31. Each target is positioned in a recessed portion of a support bracket 50 with each recessed portion having an inclined surface (e.g. 12°) for receiving a planar surface of each of the targets in proper alignment for reception of the electron beam along the nominal beam lines 61 and optimum direction of the emitted X-ray beams from the targets. The support bracket 50 is fastened to the system frame 51 by means of bolt 52. Each target segment is maintained against the inclined surface of the recessed portion by a threaded bolt 55. Each bolt 55 is threadably received in a bore through the support bracket 50 with a lock nut 57 provided to maintain the bolt in the desired pressure engagement with the spacer 53. The targets can be cooled by heat conduction to the support bracket. Coolant lines can be provided in the support structure to facilitate heat removal.

Advantageously, the targets 28–31 are oriented in the support bracket 50 so that the support bracket between targets is protected from the electron beam as shown by the shaded portion 58. Thus, heating of the support bracket is minimized.

FIG. 6 is a section view of a portion of the support bracket 50 illustrating an alternative embodiment of fastening means for the target 28. In this embodiment the spacer 73 has an inclined surface to engage a surface of the target segment 28, and another surface engages an opposing wall of the recessed portion.

The target segments are readily replaced in the support bracket as required for maintenance thereby permitting exchange of targets in the field. Further, the inclined surface of the recessed portion readily receives the target segments in proper alignment with the electron beam for X-ray generation. Target segments of varying thickness are readily accommodated using the spacer in the clamping arrangement in accordance with the invention. The entire target structure can be electrically insulated from the rest of the system by using an insulative layer such as mica between the support bracket and the mounting surface. Further, the clamping method allows for thermal expansion of the target strips as they heat during operation.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. For use in a high speed multiple section computed-tomographic X-ray transmission scanner in which X-rays are generated by directing an electron beam at an X-ray generating target, a target structure comprising
   a heat conducting support bracket having a support surface orientated at a selected angle with respect to the axis of an electron beam, said support bracket including a recessed portion and said support surface being formed in said recessed portion,
   a target member positioned in said recessed portion and having a substantially planar surface in engagement with said support surface, and
   clamp means for maintaining said target member in engagement with said support surface, said clamp means including a bolt attached to said support bracket and extending into said recessed portion and spaced from said support surface for pushing said surface of said target member in pressure engagement with said support surface.

2. A target structure as defined by claim 1 and further including spacer means between and engaged by said target member and said bolt.

3. A target structure as defined by claim 1 wherein said target member is arcuate.

4. A target structure as defined by claim 3 wherein said target structure comprises one segment of a larger target.

5. A target structure as defined by claim 1 wherein said target member comprises solid tungsten.

6. A target structure as defined by claim 1 wherein said target member comprises a layer of tungsten material.

7. An apparatus for obtaining an X-ray absorption distribution of an object comprising:
   an evacuated envelope having a longitudinal axis, said envelope including a cylindrical end portion and a conical semi-circular end portion,
   an electron gun disposed axially at the cylindrical end and projecting an electron beam,
   a focus coil disposed at the cylindrical portion to receive and focus said beam,
   bending coils following the focusing coil adapted to receive said beam and direct it into the conical end section and scan the beam along the segment of a circle,
   a plurality of adjacent target rings disposed at the end of said conical section to receive said electron beam and generate X-rays in response thereto, each of said target rings comprising
   a heat conducting support bracket having a support surface orientated at a selected angle with respect to the axis of an electron beam, said support bracket including a recessed portion and said support surface being formed in said recessed portion, a target member positioned in said recessed portion and having a substantially planar surface in engagement with said support surface, and clamp means for maintaining said target member in engagement with said support surface, said clamp means including a bolt attached to said support bracket and extending into said recessed portion and spaced from said support surface for pushing said surface of said target member in pressure engagement with said support surface, a source collimator adjacent each of said target rings to intercept said X-ray and form a fan-shaped X-ray beam which rotates as the electron beam is moved along the corresponding target ring thereby forming a plurality of fan-shaped X-ray beams to scan a plurality of adjacent sections, at least one for each target ring, and a plurality of detectors mounted opposite the target ring, said detectors arranged to form an array which is a segment of a circle; and detector collimators serving to direct the beam onto selected ones of said detectors for each target ring.

8. Apparatus as defined by claim 7 and further including spacer means between and engaged by said target member and said bolt.

* * * * *